(12) United States Patent
Bauer

(10) Patent No.: US 11,324,628 B2
(45) Date of Patent: May 10, 2022

(54) HYGIENE PRODUCT, IN PARTICULAR MENSTRUAL CUP WITH AN ERGONOMIC SHAPE

(71) Applicant: FUN FACTORY GMBH, Bremen (DE)

(72) Inventor: Dirk Bauer, Bremen (DE)

(73) Assignee: FUN FACTORY GMBH, Bremen (DE)

( * ) Notice: Subject to any disclaimer, the term of this patent is extended or adjusted under 35 U.S.C. 154(b) by 173 days.

(21) Appl. No.: 16/480,650

(22) PCT Filed: Jan. 25, 2018

(86) PCT No.: PCT/EP2018/051852
§ 371 (c)(1),
(2) Date: Jul. 24, 2019

(87) PCT Pub. No.: WO2018/138207
PCT Pub. Date: Aug. 2, 2018

(65) Prior Publication Data
US 2019/0358077 A1   Nov. 28, 2019

(30) Foreign Application Priority Data
Jan. 25, 2017  (DE) ..................... 10 2017 101 383.0

(51) Int. Cl.
*A61F 5/455*  (2006.01)
(52) U.S. Cl.
CPC ... *A61F 5/4553* (2013.01); *A61M 2210/1475* (2013.01)

(58) Field of Classification Search
CPC combination set(s) only.
See application file for complete search history.

(56) References Cited

U.S. PATENT DOCUMENTS 1,891,761 A * 12/1932 Goodard ............... A61F 5/4553
                                                             604/330
1,996,242 A *  4/1935 Hagedorn ............. A61F 5/4553
                                                             604/330
(Continued)

FOREIGN PATENT DOCUMENTS

CA       1277884 C      12/1990
CN       86 1 07000 A    7/1987
(Continued)

OTHER PUBLICATIONS

Fun Factory GmbH: "Fun Cup by Fun Factory Produktvideo—deutsch", Aug. 29, 2017, XP054978191, https://wvww.youtube.com/watch?v=YT7Np8tTJS4.
(Continued)

*Primary Examiner* — Guy K Townsend
(74) *Attorney, Agent, or Firm* — Seed IP Law Group LLP

(57) ABSTRACT

The disclosure relates to a hygiene product, in particular a menstrual cup, having a cup body comprising a cup wall defining a receiving space using an inner surface, the cup body comprising on a first end an opening opening into the receiving space, the opening having an edge, and at a second end, a bottom opposite the opening, and the cup body comprising a generally conical shape, tapering towards the bottom and terminating in a tip. The hygiene product is characterized in that the cup body is rotationally asymmetric and a central axis of the cup body runs curved.

26 Claims, 4 Drawing Sheets

(56) References Cited

U.S. PATENT DOCUMENTS

| | | | | |
|---|---|---|---|---|
| 2,089,113 A | * | 8/1937 | Chalmers | A61F 5/4553 604/330 |
| 2,321,340 A | * | 6/1943 | Waterbury | B29C 70/70 264/250 |
| 2,534,900 A | * | 12/1950 | Chalmers | A61F 5/4553 604/330 |
| 2,616,426 A | * | 11/1952 | Gordon | A61F 5/4553 604/330 |
| 3,128,767 A | * | 4/1964 | Nolan | A61F 6/08 604/330 |
| 3,216,422 A | * | 11/1965 | Steiger | A61F 6/08 604/330 |
| 3,404,682 A | * | 10/1968 | Waldron | A61F 13/266 604/330 |
| 3,626,942 A | * | 12/1971 | Waldron | A61F 5/4553 604/330 |
| 3,841,333 A | * | 10/1974 | Zalucki | A61F 5/4553 604/330 |
| 3,845,766 A | * | 11/1974 | Zoller | A61F 5/4553 604/330 |
| 4,198,965 A | * | 4/1980 | Strickman | A61F 6/08 128/832 |
| 4,381,771 A | * | 5/1983 | Gabbay | A61F 6/08 128/836 |
| 4,799,929 A | * | 1/1989 | Knowles | A61F 5/4553 604/331 |
| 4,848,363 A | * | 7/1989 | Cattanach | A61F 5/4553 128/834 |
| 4,961,436 A | * | 10/1990 | Koch | A61F 6/08 128/834 |
| D323,212 S | * | 1/1992 | Crawford | A61F 5/4553 D24/121 |
| 5,295,984 A | * | 3/1994 | Contente | A61K 9/0036 604/317 |
| 5,827,248 A | * | 10/1998 | Crawford | A61F 5/4553 604/328 |
| 5,928,249 A | * | 7/1999 | Saadat | A61B 17/42 606/119 |
| 5,947,992 A | * | 9/1999 | Zadini | A61F 13/2045 606/193 |
| 6,126,616 A | * | 10/2000 | Sanyal | A61B 10/0291 128/834 |
| 6,168,609 B1 | * | 1/2001 | Kamen | A61F 5/4553 600/573 |
| 6,241,846 B1 | * | 6/2001 | Contente | B29C 65/7867 156/378 |
| 6,264,638 B1 | * | 7/2001 | Contente | A61F 5/4553 604/285 |
| 6,332,878 B1 | * | 12/2001 | Wray | A61F 5/4553 604/328 |
| 7,845,355 B2 | * | 12/2010 | Moench | A61F 6/08 128/833 |
| 8,690,847 B2 | * | 4/2014 | Norman | A61F 5/4553 604/330 |
| D746,452 S | | 12/2015 | Petrova | |
| 9,357,982 B2 | * | 6/2016 | Edmunds | A61B 10/02 |
| D760,897 S | * | 7/2016 | Teo | A61F 5/4553 D24/141 |
| D832,438 S | * | 10/2018 | Brockway | A61F 5/4553 D24/141 |
| D836,196 S | * | 12/2018 | Ahn | A61F 5/4553 D24/141 |
| D841,808 S | * | 2/2019 | Drach | B29C 70/70 D24/141 |
| D852,361 S | * | 6/2019 | Sedic | A61F 5/4553 D24/141 |
| D852,362 S | * | 6/2019 | Sedic | A61F 5/4553 D24/141 |
| D864,390 S | * | 10/2019 | Sedic | A61B 5/6847 D24/141 |
| D892,324 S | * | 8/2020 | Yi | A61F 5/4553 D24/141 |
| D894,386 S | * | 8/2020 | LeClerc | A61F 6/08 D24/141 |
| D895,798 S | * | 9/2020 | Newman | A61F 5/4553 D24/141 |
| D895,799 S | * | 9/2020 | Newman | A61F 5/4553 D24/141 |
| D895,800 S | * | 9/2020 | Knox | A61F 5/4553 D24/141 |
| 2008/0077097 A1 | * | 3/2008 | Chambers | A61F 5/4553 604/330 |
| 2008/0200888 A1 | * | 8/2008 | Gooch | A61F 5/4553 604/330 |
| 2010/0242968 A1 | * | 9/2010 | Vean | A61F 6/08 128/830 |
| 2010/0312204 A1 | * | 12/2010 | Sheu | A61F 6/08 604/330 |
| 2013/0110060 A1 | * | 5/2013 | Shihata | A61F 5/4553 604/330 |
| 2015/0164680 A1 | * | 6/2015 | Chen | A61F 5/4553 604/330 |
| 2016/0278988 A1 | * | 9/2016 | Knox | A61F 15/005 |
| 2017/0189222 A1 | * | 7/2017 | Lin | A61F 5/4553 |
| 2018/0028350 A1 | * | 2/2018 | Wilson | A61F 5/4553 |
| 2018/0199874 A1 | * | 7/2018 | Hwang | A61B 5/6847 |
| 2018/0214298 A1 | * | 8/2018 | Medas | A61F 5/4553 |
| 2019/0021898 A1 | * | 1/2019 | Ahn | A61F 5/441 |
| 2019/0083296 A1 | * | 3/2019 | Miller | A61F 5/4553 |
| 2019/0282350 A1 | * | 9/2019 | Conti | A61F 2/0095 |
| 2019/0314191 A1 | * | 10/2019 | Bobarikin | A61F 5/4553 |
| 2019/0336318 A1 | * | 11/2019 | Kubo | A61F 5/4553 |
| 2019/0358077 A1 | * | 11/2019 | Bauer | A61F 5/4553 |

FOREIGN PATENT DOCUMENTS

| | | |
|---|---|---|
| CN | 2267780 Y | 11/1997 |
| CN | 202235939 U | 5/2012 |
| CN | 204971787 U | 1/2016 |
| CN | 105662689 A | 6/2016 |
| CN | 106073976 A | 11/2016 |
| RU | 118 862 U1 | 8/2012 |
| WO | 2006/058409 A1 | 6/2006 |
| WO | 2014/056257 A1 | 4/2014 |

OTHER PUBLICATIONS

Produktprasentation, "Luneale: Une nouvelle generation de coupe menstruelle pour simplifier la vie des femmes," dated Sep. 15, 2015, http://www.lacupluneale.com/wp-content/uploads/2015/10/CpProlancement.pdf.

\* cited by examiner

HYGIENE PRODUCT, IN PARTICULAR MENSTRUAL CUP WITH AN ERGONOMIC SHAPE

BACKGROUND

Technical Field

The disclosure relates to a hygiene product, in particular menstrual cup, having a cup body comprising a cup wall defining a receiving space using an inner surface, the cup body comprising at a first end an opening into the receiving space opening, the opening having an edge, and at the second end a bottom opposite the opening, and the cup body comprising a generally conical shape, tapering towards the bottom and terminating in a tip.

Description of the Related Art

Menstrual cups of the type mentioned above exist on the market in many ways. In general, such menstrual cups are characterized by a cup body which is generally formed conical or bell-shaped, comprising an opening on a first side and opening into a point on a second side. The tip is usually provided with a pin-shaped projection or stem, which serves as a handle. The edge bounding the opening is usually rounded and reinforced to spread open the cup body.

The pin or stem is usually provided with a structuring, for example, in the shape of circumferential ribs, in order to better grip this. Also known are pins on which threads are disposed, rings or other gripping elements.

Typical menstrual cups are implemented rotationally symmetrical. This has the purpose and advantage of simplifying insertion. When inserted, the menstrual cup is compressed, that is, folded, so that it comprises a substantially U-shaped contour at the edge. It is then inserted into the female vagina towards the uterus. Due to the reinforced edge, the menstrual cup then regains its original shape and is capable of receiving fluid in the receiving space. For changing or cleaning, the menstrual cup this is then gripped on the pin with two fingers and pulled out. To avoid a negative pressure when recovering the shape or when removing the menstrual cup, said menstrual cup usually comprises vents, which are located in the region of the upper edge.

Such a menstrual cup is disclosed in WO 2006/058409 A1.

A similar menstrual cup having a slightly longer pin, which is also suitable for cutting and thus adjusting the pin length to the respective person, is disclosed in U.S. Pat. No. D746,452 S.

A very early publication of a menstrual cup is disclosed in U.S. Pat. No. 2,534,900. The menstrual cup proposed therein does not comprise a completely rotationally symmetrical shape but has a projection on one side in the direction of the lower tip. A back of the substantially conical or bell-shaped cup body of U.S. Pat. No. 2,534,900 extends substantially straight in the direction of the tip and only then in a rather sharp curvature in the direction of the tip. The projection is thus formed in the manner of a kind of fin. This is to prevent a twisting of the menstrual cup.

A further menstrual cup intended to improve the fit is disclosed in CN 204971787 U. The substantially rotationally symmetrical menstrual cup disclosed therein is slanted in the region of the upper opening. The edge in this case is not implemented reinforced as in the other menstrual cups known in the prior art, but has a soft collar extending radially inwardly. A flowing out of received liquid should be avoided through this collar.

In addition to the problem of correct positioning, there is a further problem with the removal of the menstrual cup. If said menstrual cup is pulled out, for example, only on a thin pin, there is a risk that this slips away from an operator after the removal or folds over at the pin and received liquid can thus be easily spilled.

This problem is also partially addressed by the collar facing radially inwardly disclosed in CN 204971787 U.

Other solutions suggest a valve or discharge opening in the region of the tip. This is proposed, for example, in CN 106073976 A or WO 2014/056257 A1. An emptying is theoretically possible in such menstrual cups even in the inserted state, namely by opening the valve.

But even such solutions have proved impractical, in particular since the valve can open accidentally.

BRIEF SUMMARY

The object of the present disclosure is therefore to provide a hygiene product, in particular menstrual cup, which is improved in fit, easy to handle and can be removed safely and safely.

This object is achieved in a hygiene product of the type mentioned above in that the cup body is rotationally asymmetric and a central axis of the cup body runs curved.

The disclosure is based on the idea that a rotationally asymmetric shape is better suited for a good fit of the hygiene product within the vagina. As a result, the outer contour of the hygiene product can be better adapted to the anatomical conditions and optimize the fit. It has been found that it is not sufficient to provide only an external web, as is known in the prior art, or to dispose the opening at an angle relative to a central axis, as is also known in the prior art. Rather, the disclosure is based on the idea that the menstrual cup must be implemented curved overall, that is, that the central axis which extends centrally through the body of the hygiene product is curved. The central axis runs first from the center of the opening, through the receiving space and finally through the tip. The central axis here is to be understood as the respective connection between centers of sections along the central axis from the center of the opening to the tip.

The risk of twisting of the hygiene product in use does not actually exist in the design of the disclosure. As such, the rotationally asymmetric shape already prevents twisting, since, due to the curvature, the outer contour of the hygiene product is adapted to the inner contour of the vagina. As a result, a self-positioning in the motion takes place instead.

Also, the problem of positioning does not exist. Although it is irrelevant in rotationally symmetrical menstrual cups at which circumferential point this is folded in for insertion, however, in the case of a rotationally asymmetrical menstrual cup, it is clear to the operator at which point it should be pressed in.

Also, the removal is simplified since the central axis is curved. The curvature makes it possible to keep the plane of the opening substantially horizontal while the menstrual cup is removed. During removal, a central axis of the vagina is also curved, so that the central axis of the vagina and the central axis of the cup body run substantially coaxial. The removal is greatly simplified in this way, and spillage can be avoided. The central axis is preferably curved over a segment in a range of 30° to 90°, preferably 45° to 80°. A radius of curvature is preferably in a range of 2 cm to 30 cm, wherein the radius of curvature can vary along the central axis.

The cup body terminates at the tip and preferably has no pin or stem. It has been found that the hygiene product is easier to grasp by a stem, but there is a risk of dumping when being taken out. All the more so, when the stem is grasped only at the extreme end. However, if the hygiene product does not comprise a stem, an operator is induced to grasp the sanitary product at the tip of the cup body, thereby achieving a more secure grip that is more resistant to dumping.

According to a first preferred embodiment, the cup body comprises a plane of symmetry and is implemented mirror-symmetrical with respect to this plane of symmetry. The cup body is rotationally asymmetric, but mirror-symmetrical. This also corresponds to the natural shape of the inner vaginal wall, so that an adaptation of the cup body to the vagina is improved and thus the fit of the hygiene product is improved in use. Furthermore, this also simplifies the positioning, since a folding of the menstrual cup is simplified. The folding is preferably made along the axis of symmetry, so that in the U-shaped folding position, the plane of symmetry runs between the two legs of the U.

Furthermore, it is preferred that a first segment of the cup wall runs along the plane of symmetry from the edge of the opening to the tip on the outside substantially in the shape of a partial circle. This first segment of the cup wall can also be referred to as a back, as it shows in the inserted state in the direction of the back of the user. As a result, the curvature is supported and an ergonomic fit of the hygiene product is achieved.

Furthermore, it is preferred that a second segment of the cup wall along the plane of symmetry from the edge of the opening to the tip defines a substantially convex-concave shape. That is, the second segment of the cup wall initially runs in a convex shape and then concave to the tip. This also supports the curvature. The cup body thus receives a slightly bulbous or bell-shaped shape, but is generally implemented conical. The shape of the cup body can also be compared with a drop that runs crooked towards the end of the drop.

Furthermore, it is preferred that the cup body has a bulbous shape in which the cup body tapers slightly in the region of the opening. As a result, on the one hand, the positioning is simplified since the position is held not only by the edge, but also and substantially by the side walls. On the other hand, a spillage of received liquid is effectively avoided by the cup body tapering slightly in the region of the opening.

According to a further preferred embodiment, the tip comprises a generally conical shape. As a result, the tip is initially harder to grip than a straight stem. However, a conical tip causes an operator to grip the cup body firmly, which in turn prevents dumping after the removal. An initially difficult gripping of the cup body thus achieves safer gripping as an end effect and prevents dumping.

Preferably, the tip is implemented as a thickening in the cup wall. This makes it possible to grip the tip firmly without compressing it too much. Furthermore, this makes it possible to compress the cup wall above the tip, that is, adjacent to the tip between the tip and the opening and thus to grip behind the thickening that forms the tip. As a result, a particularly safe removal and a particularly good protection against dumping is achieved.

The thickening preferably corresponds approximately to three to six times, preferably four to five times the wall thickness of the cup wall. The thickness of the thickening is measured at the thickest point of the thickening. It has been shown that a thickening in this region leads to a particularly safe and easy gripping, without, however, interfering with the use.

More preferably, the tip comprises a length in a range of 5 to 12 mm. Such a range has proven to be suitable for making the tip, which is formed by the thickening, easy to grip from behind. An operator can well feel the thickened tip with such a size and grip behind it, so as to remove the hygiene product.

Preferably, the cup wall transitions into the tip without kinking. This also increases the stability. A plurality of menstrual cups is known in the prior art, which indeed comprise a conical or bell-shaped shape, but in which the stem extends with a kink, in particular a kink at approximately a right angle, from the cup wall in the region of the tip. A transition without kinks, on the one hand, slightly increases the rigidity in the region, on the other hand, the cleaning of the hygiene product is simplified.

In a preferred development, the cup wall comprises a structuring on the outside in the region of the tip. Since the menstrual cup is grasped in the region of the tip to remove it, such a structuring is preferred in order to increase the friction between the grasping fingers and the cup body. Preferably, the remaining surface of the cup wall is implemented externally without structuring. Cups are also known in the prior art which comprise ribs distributed externally over the entire body. However, structuring that is not used for grasping tends to result in more difficult removal. It is therefore preferred that the cup wall comprises structuring externally only in the region of the tip.

The structuring is preferably implemented as a plurality of projections. Although circumferential ribs are conceivable, these, however, can lead to a seal of the cup body against the inner surface of the vagina, which in turn can cause a negative pressure generation when taken out. The individual projections are preferably separated. In a variant, the projections are each implemented annular. That is, a plurality of rings, such as circles, or other shapes are implemented raised in the region of the tip. In a particularly preferred variant, the projections are implemented annular, and have a shape that resembles cores of a strawberry. As such, the cup body comprises an approximately strawberry-shaped shape, and by implementing the projections as cores of the strawberry, this association is enhanced. As a result, the hygiene product additionally receives an attractive appearance, which has a playful effect and arouses less associations with sanitary products.

According to a further preferred embodiment, the edge of the opening is reinforced. Such a reinforcement serves in particular to bring the cup body into a spread-open shape after positioning, so that the opening actually stays open, so that the receiving space can receive liquid. Furthermore, the reinforcement serves to hold the cup body in this position, so that a positioning of the menstrual cup is maintained in the vagina.

Preferably, this reinforcement is implemented as a thickening in the cup wall. The thickening preferably extends radially inward from the cup wall, so that the receiving space is generally implemented bulbous. However, a radially outwardly projecting ring has rather proved to be disadvantageous.

Preferably, the edge is implemented so that it drops at an angle to the receiving space. This leads to an improved fluid reception. The edge can comprise a relatively small radius in the segment where it transitions into the outer wall of the cup so as to enable a close fit to the skin. As a result, a tightness is achieved without simultaneously applying too much pressure. This also significantly improves the wearing comfort.

Preferably, the opening is substantially circular. A circular opening provides a relatively high stability in the case of the reinforcement of the edge compared to other shapes and also corresponds to the anatomical conditions at the positioning site.

In a further preferred embodiment, the cup wall comprises a substantially constant wall thickness between the edge of the opening and the tip. A substantially constant wall thickness also achieves a substantially uniform rigidity, and a pleasant fit and the wearing comfort are improved. The only stiffened regions in this embodiment are the edge and the tip.

Preferably, the cup body is integrally implemented. A one-piece implementation improves the wearing comfort and the cleaning of the product is also simplified. There are no seams, joints or the like provided between different components, which makes the cleaning substantially easier.

In a particularly preferred embodiment, the cup body is formed of a silicone having a Shore hardness in a range of 18 to 60, in particular 30 to 50, preferably 35 to 45. Silicone is particularly suitable for the formation of a menstrual cup, because, on the one hand, silicone is particularly well tolerated by the skin, on the other hand, its structure provides sufficient flexibility but also rigidity in order to a enable positioning. The durability of the silicone is high, so that the hygiene product can be reused frequently. A Shore hardness, in particular in a range from 35 to 45, has proven to be particularly suitable in order to resolve as much as possible the conflict of goals between the stiffness and the elasticity or flexibility of the hygiene product. Most preferably, the silicone is medical silicone. It is thus better tolerated by the skin.

Preferably, the cup body is formed from an injection molded silicone or liquid silicone. In particular, materials such as LSR (liquid silicone rubber), HTV (high-temperature cross-linked silicone rubber), or RTV (room temperature-cross-linked silicone rubber) are used. TPE or rubber are also suitable.

The cup wall preferably has a wall thickness in a range of 0.8 mm to 8.0 mm, preferably 1.0 mm to 3.0 mm, more preferably 1.5 mm to 2.5 mm. Wall thicknesses in the range of about 2.0 mm have proven particularly suitable. As a result, with an appropriate choice of material, in particular silicone material, restoring forces can be achieved which result, on the one hand, in the hygiene product being comfortable to wear, on the other hand maintaining both its position and a non-collapsed state, which is important in order to carry out its function adequately.

Preferably, the cup wall comprises a restoring force against compression in a range of 4 N to 15 N, preferably 5 N to 10 N, more preferably 6 N to 10 N. The edge of the cup wall can also comprise a restoring force against a compression in a range of 6 N to 15 N. Restoring force against compression means the force required to compress the cup body on two opposite sides so that the opposite sides just touch each other.

BRIEF DESCRIPTION OF THE SEVERAL VIEWS OF THE DRAWINGS

The disclosure is explained in more detail with reference to an embodiment with reference to the accompanying figures. Shown are.

DETAILED DESCRIPTION

Figure 1:
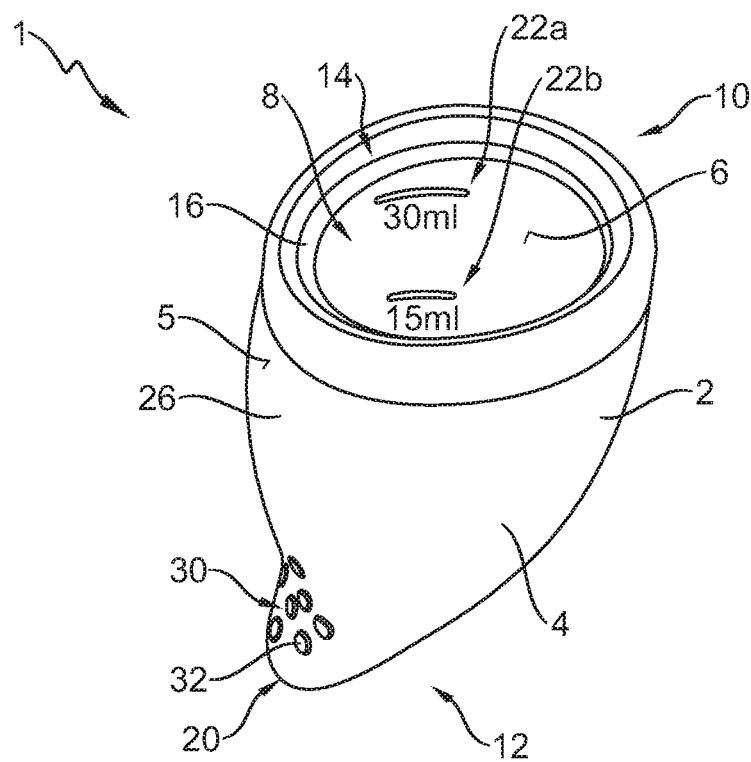
FIG. 1 is a first perspective view of the hygiene product.
Figure 2:
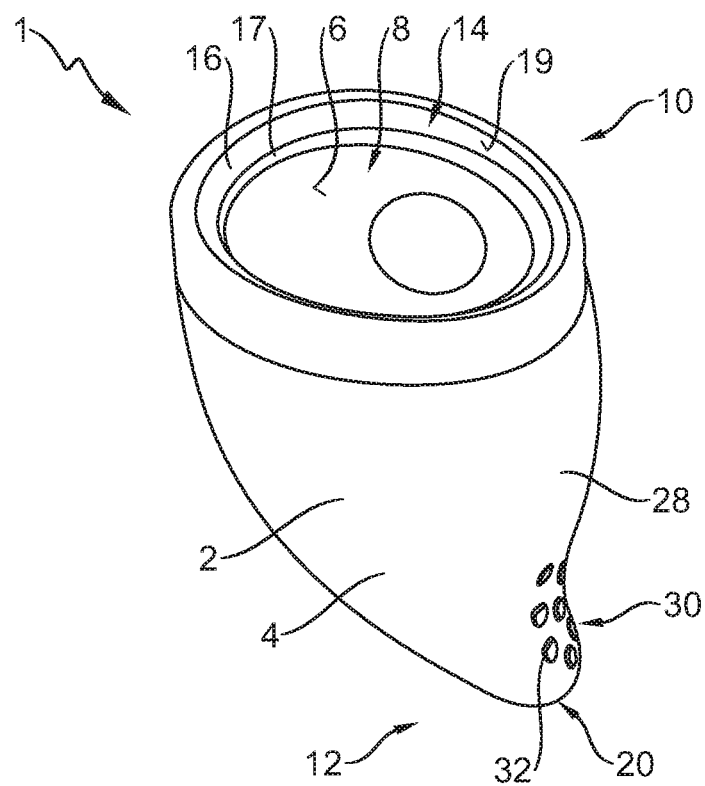
FIG. 2 is a second perspective view of the hygiene product of FIG. 1.

According to FIG. 1, a hygiene product, which is implemented here as a menstrual cup 1, comprises a cup body 2, which has a cup wall 4, which defines a receiving space 8 using an inner surface 6. The cup body 2 comprises a first end 10 and a second end 12. The cup body 2 has an opening 14 at the first end 10, said opening being bounded by an edge 16. The cup body 2 comprises a bottom 18 at the opposite end 12 (see FIG. 4).

Overall, the cup body 2 is formed in a conical shape or bell-shaped shape and tapers from the opening 14 in the direction of the second end 12 and terminates there in a tip 20.

Figure 6:
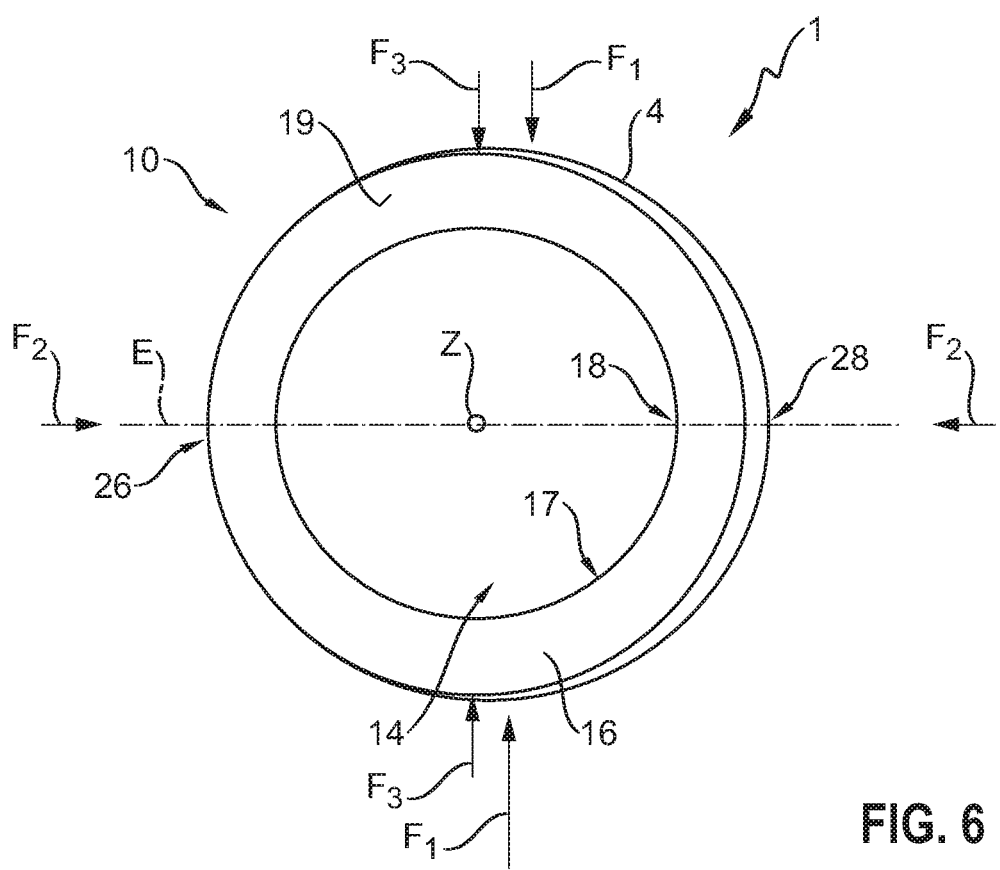
FIG. 6 is a plan view of the hygiene product of FIG. 3 from above.

As can be seen in particular from FIGS. 1 to 4, the cup body 2 is rotationally asymmetrical, but mirror-symmetrical. The central axis Z (see FIGS. 4 and 7) is curved, but lies in the plane of symmetry E (see FIG. 6). The central axis Z first passes through the center of the opening 14, then through the receiving space 8 and finally out of the proximal end of the tip 20. The central axis is straight, however, for rotationally symmetrical cup bodies.

The cup body 2 is much better adapted to the anatomy of the female vagina than previous menstrual cups 1 as a result of this curvature of the cup body.

Figure 7:
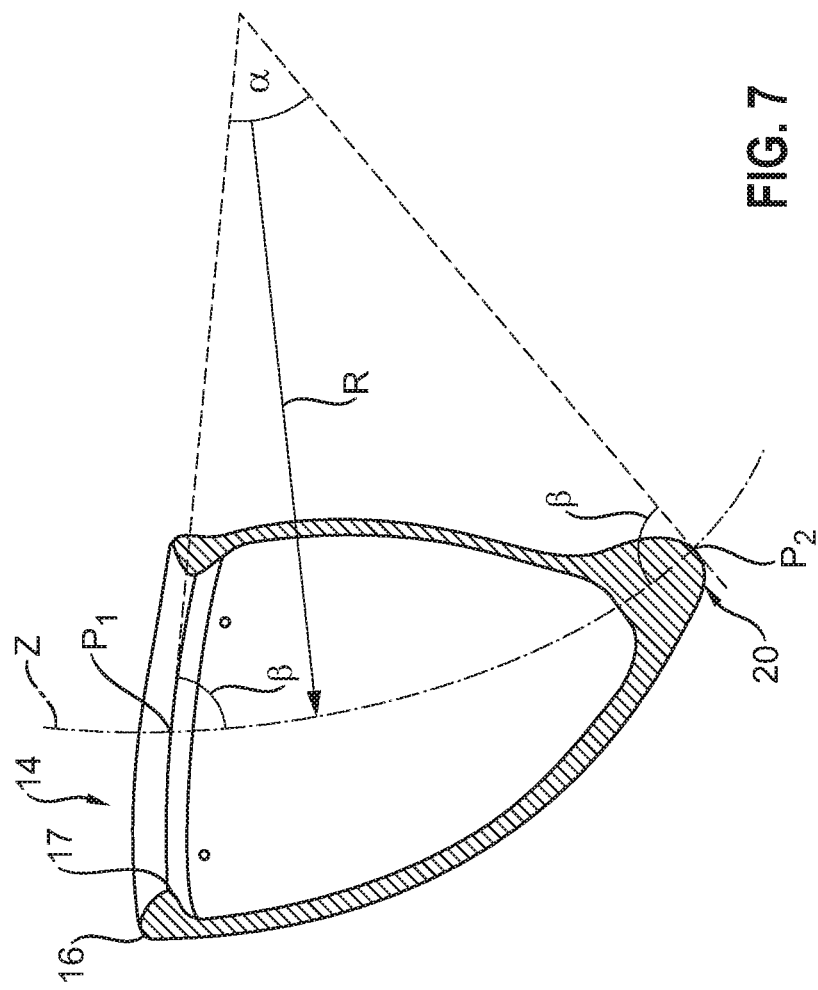
FIG. 7 is a view as in FIG. 4, illustrating the curvature of the central axis.

The course of the curvature of the central axis Z is illustrated by geometric relationships in FIG. 7. The central axis Z runs from a first intersection point $P_1$ with a plane of the opening 14 that extends through the ridge 17 of the edge 16, to a second intersection point $P_2$, the proximal point of the tip 20. The planes perpendicular to the central axis Z at these points $P_1$ and $P_2$ (see angle β) enclose an angle α with each other. The angle α is in a range of 20° to 90°, and in the present embodiment, approximately in the range of 45°. The radius of curvature R can vary along the segment of the central axis Z between the points $P_1$ and $P_2$, and is about 8.5 cm on average in this embodiment. However, the radius R is dependent on the size of the menstrual cup 1, and can be, on average, in a range of 5 cm to 20 cm, or outside this range.

The receiving space 8 is used for receiving liquid when the menstrual cup 1 is inserted for use. Dimensions 22a, 22b are provided on the inner surface 6 in this exemplary embodiment (see FIG. 1), said dimensions being used to determine the amount of liquid received in the receiving space 8.

The receiving space 8 is generally implemented bulbous and is bounded by the edge 16 in the region of the opening 14. The edge 16 is implemented reinforced, as a thickening, which extends radially inwardly. In this respect, the edge 16 has a radially projecting ridge 17, which represents a radial constriction. A surface 19, which runs from the edge 16 to the ridge 17, that is, substantially from the outer shell surface 5 of the cup wall 4 to the ridge 17, is implemented at an angle with respect to the central axis Z. This ensures that, with reference to FIGS. 3 and 4, liquid draining from above is safely received in the receiving space 8 and does not pass outside the menstrual cup 1 in the region of the shell surface 5.

A stabilization of the shape of the cup body 2 is also achieved due to the thickening in the edge 16. As can be seen in particular from FIG. 6, the opening 14 comprises a substantially circular contour. The thickening in the region of the edge serves to spread open this opening 14, so that the menstrual cup 1 is functional. It is important that the menstrual cup 1 does not collapse in the inserted state, but is spread out as far as possible, so that liquid can be effectively collected in the receiving space 8.

The bottom 18 is closed and does not comprise a passage opening. In departure from the prior art, the menstrual cup 1 according to the present embodiment does not comprise a valve or the like.

The cup wall 4 extends from the edge 16 in the direction of the tip 20 and opens into it. The cup wall 4 thereby transitions without kinks into the tip 20, both on the inner surface 6 and on the outer shell surface 5. A first segment 26 of the cup wall 4 along the plane of symmetry E from the edge 16 of the opening 14 to the tip 20 runs substantially partially circular. As can be seen in particular from FIGS. 3 and 4, the cup wall 4 transitions continuously in the segment 26 in the tip 20; there is no discontinuity. The slope remains substantially constant, at least there is no change in the direction of slope. The segment 26 is formed completely convex.

The cup wall 4 comprises a segment 28 on the opposite side of the cup body 2 along the plane of symmetry E. The segment 28 is implemented corresponding to the segment 26 and also extends from the edge 16 to the tip 20. The segment 28 comprises a first partial segment 28a, which is formed convex, and a second segment 28b, which is implemented concave. The segment 28 thus comprises an overall convex-concave shape and also flows steadily into the tip 20. At the tip 20, a convex region 21 adjoins the concave region 28b again, which forms part of the tip 20. This shape reinforces the curvature of the central axis Z (see FIG. 7) and at the same time forms a bulbous shape of the receiving space 8. Furthermore, this implementation supports the point-like configuration of the tip 20.

The tip 20 is implemented as a thickened region of the cup wall 4. The cup wall 4 comprises a total wall thickness $h_1$, which is substantially constant except for the edge 16 and the tip 20. The tip 20 is thickened and comprises a maximum thickness $h_2$. The maximum thickness $h_2$ corresponds approximately to four times the wall thickness $h_1$. As a result, the tip 20 is substantially stronger than the cup wall 4 in the radial direction.

If, after use, the menstrual cup 1 is taken out, an operator can grasp the menstrual cup 1 in the region of the tip 20.

The operator can grab the tip 20 from both sides in this case. In order to increase the friction between the fingers and the menstrual cup 1, the menstrual cup 1 comprises a structuring 30 in the region of the tip 20. The structuring 30 is disposed exclusively in the region of the tip in order to increase friction only there. In particular, no structuring is provided in the overlying segment in the direction of the opening 14 of the menstrual cup 1; rather, the shell surface 5 is implemented in this region, in about the upper two-thirds or the upper half of the menstrual cup, without structuring. The shell surface 5 is substantially smooth in this region. The wearing comfort is further improved as a result. It has been shown that a structuring in the upper region can be a hindrance, in particular when being taken out, which on the one hand is unpleasant, on the other hand, can easily lead to spillage of received liquid.

The structuring 30 is implemented as a plurality of projections 32, which are shaped like cores of strawberries. Due to this type of projections 32 and the curved shape of the cup body 2, there is an overall association of the menstrual cup 1 with a strawberry.

When removing, it is also possible that an operator not only grips the tip 20, but the fingers apply in the region just behind the tip 20, thus slightly above the concave partial segment 28b, and so compresses the cup body 2 there. Since the cup wall 4 is flexible, it can be compressed there; the edge 16 further maintains the upper shape of the cup body 2 without collapsing. By compressing the cup wall 4 just above the concave partial segment 28b, it is possible to grip behind the tip 20 so as to grip and remove the menstrual cup 1 even better. This solid grip further prevents dumping after removal, whereby received liquid remains in the receiving space 8 and is not spilled. It can also be seen in the figures that the menstrual cup 1 according to the present disclosure does not comprise a stem or pin in the region of the tip 20; rather, the tip 20 terminates substantially conical or bell-shaped as a concave nub. It has been found that the widely used stems in the prior art tend to cause the menstrual cup to dump after being removed since the stems are typically implemented as substantially cylindrical pins and comprise partially radially circumferential ribs. Such ribs are not able to increase a friction between the finger and the menstrual cup in such a way that dumping is prevented. However, the individual projections 32 lead to a uniform increase in friction, both in the axial and in the radial direction, and thus serve as a safe protection against dumping.

Figure 3:
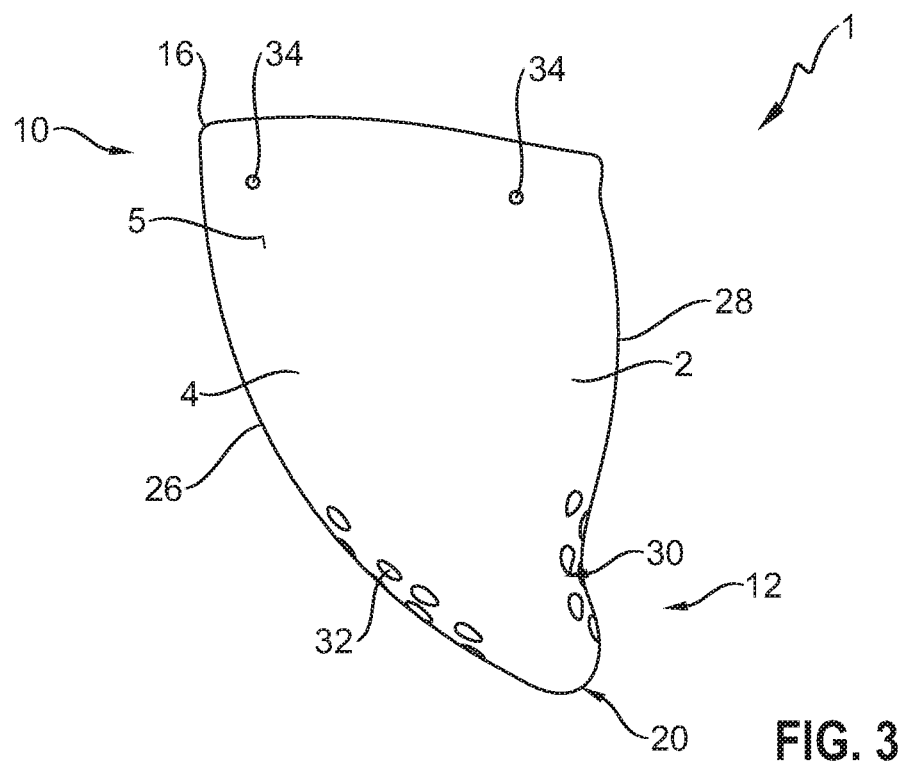
FIG. 3 is a side view of the hygiene product of FIG. 1.

As can be seen from FIGS. 3 and 4, ventilation holes 34 are provided in the upper region, just below the edge 16. These are so small that liquid that runs over the edge 16 into the receiving space 8, does not pass through them. This prevents capillary action. However, these ventilation holes 34 serve to compensate for a negative pressure. If the menstrual cup 1 is folded together and inserted, it increases the volume when spreading out by recoil of the ring 16. If the edge 16 then abuts against the skin, a negative pressure forms. However, a negative pressure in the interior of the receiving space 8 leads to a considerably more difficult removal of the menstrual cup and can also have a negative impact on wearing comfort. The ventilation holes 34 provide a connection between the interior 8 and the outer region and can cause a pressure equalization. The removal of the menstrual cup 1 is further simplified as a result.

Figure 4:
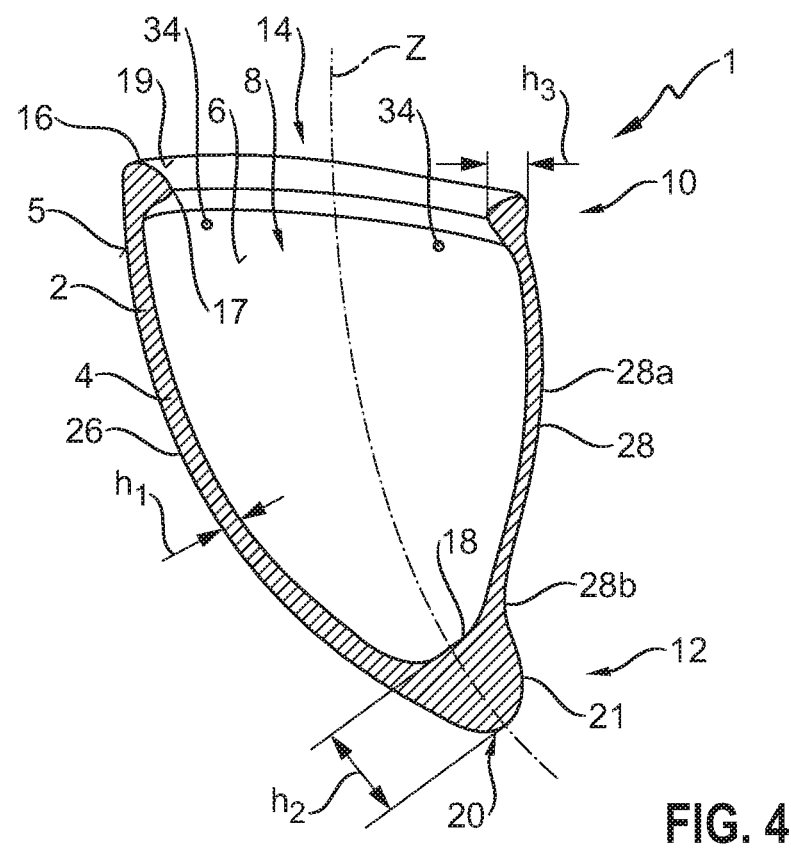
FIG. 4 is a sectional representation of the hygiene product from FIG. 3 along the plane of symmetry.
Figure 5:
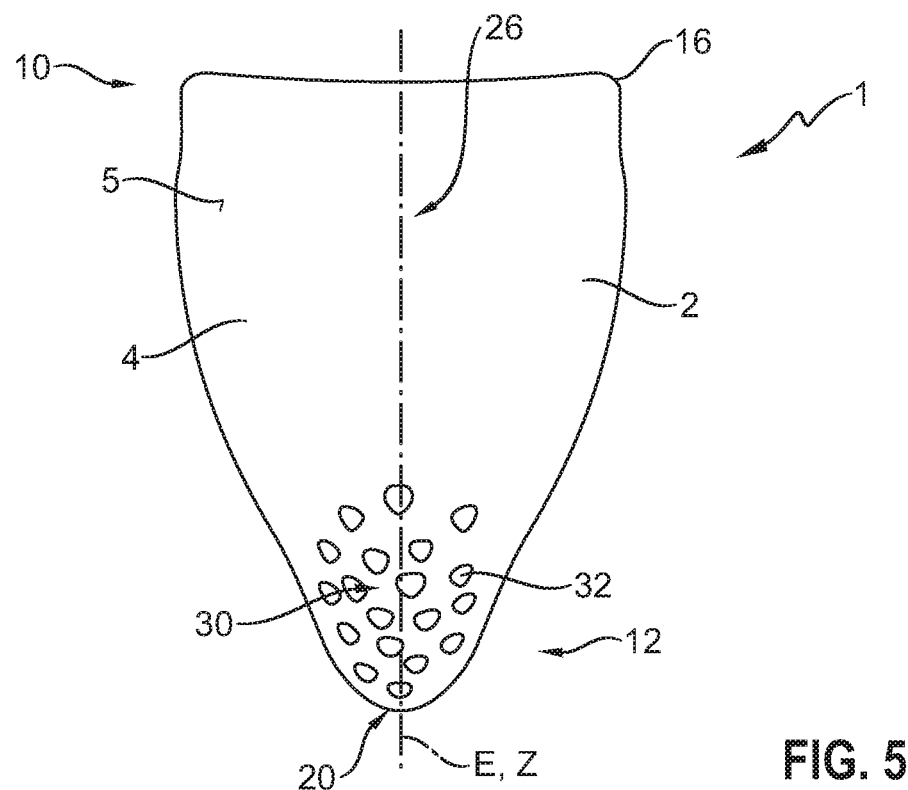
FIG. 5 is a view of the back, from the left in FIG. 3 of the hygiene product.

As can be seen in particular from FIG. 4, the menstrual cup 1 is implemented integrally as a whole. It is formed from a medical silicone material having a Shore hardness in the range of 35 to 45, in particular by means of injection molding. Medical silicone is particularly well tolerated by the skin and is suitable for this use. The Shore hardness of 35 to 45 provides sufficient flexibility for wearing comfort, but at the same time sufficient rigidity, so that the edge 16 provides a certain shape stability and the menstrual cup 1 can be safely removed at the tip 20.

Conventional silicones can also be used as an alternative to the medical silicone. Preferred materials are in particular injection molded silicone or liquid silicone. In particular, materials such as LSR (liquid silicone rubber), HTV (high-temperature cross-linked silicone rubber), or RTV (room temperature-cross-linked silicone rubber) are used. Also suitable are TPE, in particular soft TPE, or rubber.

The cup wall 4 in this embodiment has a wall thickness h1 (see FIG. 4) in a range of 1.5 mm to 2.5 mm. The edge 16 has a wall thickness h3 of 4 to 8 mm, in this embodiment about 4.5 mm.

Preferably, the cup wall 4 comprises a restoring force F1 (see FIG. 6) against compression in a range of 4 N to 15 N, preferably 5 N to 10 N, more preferably 6 N to 10 N. The restoring force F1 is measured perpendicular to the plane of symmetry E and approximately halfway between the edge 16 and the tip 20, that is, approximately in the thickest region of the cup body 2. The opening 14 and any ventilation holes 34 remain free in this case. Restoring force against compression means the force required to compress the cup body 2 at this point so that the opposite sides of the cup wall 4 just touch.

Furthermore, the edge 16 of the cup wall 4 also has a restoring force F2, F3 against a compression in a range of 6 N to 15 N. First, a first edge restoring force F2 can be measured in the plane of symmetry E, which can preferably be in a range of 8 N to 15 N, preferably 9 N to 12 N. A second edge restoring force F3 is preferably measured perpendicular to the first edge restoring force F2, and is preferably in a range of 6 N to 10 N, preferably 6 N to 8 N.

Preferably, the restoring forces F1, F2, F3 are matched to one another, so that, for example, in a first embodiment: F1 is about 6 N; F2 is about 6.3 N; F3 is about 9.6 N. In a second embodiment: F1 is about 7.6 N; F2 is about 7.0 N; F3 is about 11 N. A third embodiment can comprise the values: F1 about 9.8 N; F2 about 7.3 N; F3 about 11.3 N. It can be provided that higher restoring forces F1, F2, F3 act when there are altogether smaller cup bodies 2. In addition, it can be provided that the various embodiments are color-coded, so that the user can recognize the region of the restoring forces F1, F2, F3 on the basis of the color of the cup body 2.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A hygiene product, comprising:
a menstrual cup, including:
a cup body having a cup wall with an outer shell surface and an inner surface defining a receiving space, the cup body including:
a first end and a second end;
an opening into the receiving space at the first end of the cup body, the opening having an edge; and
a bottom opposite the opening at the second end of the cup body,
wherein the cup body has a generally conical shape, tapering towards the bottom and terminating in a tip, wherein both the inner surface and the outer shell surface transition as a smooth structure without kinks into the tip, the inner surface forming an inner contour and the outer shell surface forming an outer contour, wherein the inner contour and the outer contour smoothly diverge in the region of the tip to form a thickened region of the cup wall, wherein the thickened region of the cup wall forms the tip of the cup body, and
wherein the cup body is rotationally asymmetric and a central axis of the cup body is curved.

2. The hygiene product according to claim 1, wherein the cup body has a plane of symmetry and is mirror-symmetrical with respect thereto.

3. The hygiene product according to claim 2, wherein the cup wall includes a first section extending in a partially circular shape along the plane of symmetry from the edge of the opening to the tip on an outside of the cup wall.

4. The hygiene product according to claim 3, wherein a second section of the cup wall defines a substantially convex-concave shape along the plane of symmetry from the edge of the opening to the tip.

5. The hygiene product according to claim 1, wherein the cup body has a bulbous shape in which the cup body tapers proximate the opening.

6. The hygiene product according to claim 1, wherein the tip has a conical shape.

7. The hygiene product according to claim 6, wherein the tip is part of the cup wall and has a first thickness that is greater than a second thickness of the cup wall between the opening and the tip.

8. The hygiene product according to claim 7, wherein the first thickness is 3 to 6 times greater than the second thickness of the cup wall.

9. The hygiene product according to claim 6, wherein the tip is a solid piece of material with a length in a range of 5 to 12 mm.

10. The hygiene product according to claim 1, wherein the cup wall has a structure on an outside of the cup wall in a region of the tip.

11. The hygiene product according to claim 10, wherein the structure is a plurality of protrusions.

12. The hygiene product according to claim 11, wherein each of the plurality of protrusions are annular.

13. The hygiene product according to claim 1, wherein the edge of the opening has a reinforcement including a thickening of the cup wall extending radially inward from the cup wall.

14. The hygiene product according to claim 1, wherein the edge of the opening includes a ridge extending radially inward from the edge of the opening forming a radial constriction, the ridge including a vertex positioned between the cup wall and a top of the edge, the cup body sloping down towards the receiving space from the top of the edge to the vertex of the ridge, the cup body further sloping away from the receiving space from the vertex of the ridge to the cup wall, the ridge forming a radial inner bulge.

15. The hygiene product according to claim 1, wherein the opening is circular.

16. The hygiene product according to claim 1, wherein the cup wall has a substantially constant wall thickness between the edge of the opening and the tip.

17. The hygiene product according to claim 1, wherein the tip of the cup body is a solid piece of material integral with the cup wall, the cup wall being flexible and structured to compress in a region above the tip to enable gripping and removal of the cup body via the tip.

18. The hygiene product according to claim 1, wherein the cup body includes silicone having a Shore hardness in a range of 18 to 60.

19. The hygiene product according to claim 1, wherein the cup wall has a wall thickness in a range of 0.8 mm to 8.0 mm.

20. The hygiene product according to claim 1, wherein the cup wall has a restoring force against compression in a range of 4 N to 15 N.

21. The hygiene product according to claim 1, wherein the edge has a restoring force against compression in a range of 6 N to 15 N.

22. A hygiene product, comprising:
a menstrual cup, including:
    a cup body having a cup wall with an inner surface defining a receiving space, the cup body including:
        a first end and a second end;
        an opening into the receiving space at the first end of the cup body;
        an edge around the opening having a reinforcement including a thickening of the cup wall; and
        a bottom opposite the opening at the second end of the cup body,
    wherein the cup body has a generally conical shape, tapering towards the bottom and terminating in a tip,
    wherein the cup wall and the edge around the opening are a uniform silicone material for providing a shape stability of the edge and for maintaining a non-collapsed state of the cup wall, so that a position of the cup body is held by the edge in combination with the cup wall,
    wherein the tip is a solid portion of the silicone material with a conical shape integral with the cup wall as a thickening in the cup wall, and
    wherein the cup body is rotationally asymmetric and a central axis of the cup body is curved.

23. The hygiene product according to claim 22 wherein the receiving space of the cup body terminates at an interface between the cup wall and a top of the tip, the tip having a thickness greater than a thickness of the cup wall with the cup wall being flexible and structured to compress in a region above the tip.

24. A hygiene product, comprising:
a menstrual cup, including:
    a cup body having a cup wall with an outer shell surface and inner surface defining a receiving space, the cup body including:
        a first end and a second end;
        an opening into the receiving space at the first end of the cup body;
        an edge around the opening; and
        a bottom opposite the opening at the second end of the cup body,
    wherein the cup body has a generally conical shape, tapering towards the bottom and terminating in a tip,
    wherein the cup body is rotationally asymmetric and a central axis of the cup body is curved, and
    wherein the cup wall includes structuring implemented as a plurality of projections distributed over a circumferential portion on the outer shell surface only in a region of the tip.

25. The hygiene product according to claim 24, wherein the tip is a solid piece of material integral with the cup wall, the tip having a thickness greater than a thickness of the cup wall.

26. The hygiene product of claim 1, wherein the cup body further includes a ridge extending only radially inward from the edge of the opening of the cup body into the opening, the ridge being a thickened portion of the cup wall between the outer shell surface and the inner surface of the cup wall, the cup body further including a ridge surface from the outer shell surface to the ridge positioned at an angle with respect to the central axis of the cup body, and
wherein the cup wall further includes a first segment from the first end to the second end of the cup body on a first side of the central axis of the cup body and a second segment from the first end to the second end of the cup body on a second side of the central axis of the cup body opposite to the first side,
the first segment being completely convex and the second segment including a first portion corresponding to a portion of the cup wall defining the receiving space, a second portion corresponding to a portion of the cup wall at an interface between the receiving space and the tip, and a third portion of the cup wall corresponding to the tip, the first portion of the second segment being convex, the second portion of the second segment being concave, and the third portion of the second segment being convex.

* * * * *